US011334988B2

(12) United States Patent
Shinoda et al.

(10) Patent No.: US 11,334,988 B2
(45) Date of Patent: May 17, 2022

(54) INFORMATION PROCESSING APPARATUS, INFORMATION PROCESSING METHOD, PROGRAM, AND OBSERVATION SYSTEM FOR CELL IMAGE CAPTURE

(71) Applicant: Sony Corporation, Tokyo (JP)

(72) Inventors: Masataka Shinoda, Kanagawa (JP); Tomoya Onuma, Shizuoka (JP); Takeshi Ohashi, Kanagawa (JP); Taro Azuma, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 16/463,016

(22) PCT Filed: Oct. 19, 2017

(86) PCT No.: PCT/JP2017/037848
§ 371 (c)(1),
(2) Date: May 22, 2019

(87) PCT Pub. No.: WO2018/100913
PCT Pub. Date: Jun. 7, 2018

(65) Prior Publication Data
US 2020/0065962 A1 Feb. 27, 2020

(30) Foreign Application Priority Data
Nov. 29, 2016 (JP) .............................. JP2016-231818

(51) Int. Cl.
*G06T 7/00* (2017.01)
*G16H 10/40* (2018.01)
(Continued)

(52) U.S. Cl.
CPC ....... *G06T 7/0012* (2013.01); *G01N 15/1425* (2013.01); *G01N 15/1463* (2013.01);
(Continued)

(58) Field of Classification Search
CPC .......... G01N 15/1425; G01N 15/1463; G01N 2015/1006; G01N 2015/144;
(Continued)

(56) References Cited

U.S. PATENT DOCUMENTS 6,752,008 B1 * 6/2004 Kley ...................... G01Q 10/06
73/105
2003/0082818 A1 * 5/2003 Bahnson .................. C12Q 1/24
436/63
(Continued)

FOREIGN PATENT DOCUMENTS

EP 3192861 A1 7/2017
EP 3470510 A1 4/2019
(Continued)

OTHER PUBLICATIONS

International Search Report and Written Opinion and English translation thereof dated Jan. 16, 2018 in connection with International Application No. PCT/JP2017/037848.
(Continued)

*Primary Examiner* — James T Boylan
(74) *Attorney, Agent, or Firm* — Wolf, Greenfield & Sacks, P.C.

(57) ABSTRACT

[Object] To provide an information processing apparatus, an information processing method, a program, and an observation system with which images of cells under observation are efficiently captured.
[Solving Means] An information processing apparatus according to the present technology includes an image-capture controller unit, an image-capture area classifier unit, and an observation controller unit. The image-capture controller unit controls an image-capture mechanism to capture images of a culture vessel including a plurality of wells that house cells for each image-capture area. The image-capture area classifier unit applies image processing to the images
(Continued)

captured by the image-capture mechanism and classifies the plurality of image-capture areas into a first image-capture area of which image-capturing is continued and a second image-capture area of which image-capturing is not continued on the basis of a result of the image processing. The observation controller unit instructs the image-capture controller unit to capture an image of an image-capture area classified as the first image-capture area and not to capture an image of an image-capture area as the second image-capture area.

12 Claims, 10 Drawing Sheets

(51) Int. Cl.
| | |
|---|---|
| G16H 30/20 | (2018.01) |
| G16H 30/40 | (2018.01) |
| H04N 5/232 | (2006.01) |
| G06N 20/00 | (2019.01) |
| G01N 15/14 | (2006.01) |
| H04N 5/225 | (2006.01) |
| G01N 15/10 | (2006.01) |

(52) U.S. Cl.
CPC ............. *G06N 20/00* (2019.01); *G16H 10/40* (2018.01); *G16H 30/20* (2018.01); *G16H 30/40* (2018.01); *H04N 5/2256* (2013.01); *H04N 5/23299* (2018.08); *G01N 2015/1006* (2013.01); *G01N 2015/144* (2013.01); *G01N 2015/1493* (2013.01); *G01N 2015/1497* (2013.01); *G06T 2207/20081* (2013.01); *G06T 2207/30024* (2013.01); *G06T 2207/30072* (2013.01)

(58) Field of Classification Search
CPC ... G01N 2015/1493; G01N 2015/1497; G06N 20/00; G06T 2207/20081; G06T 2207/30024; G06T 2207/30072; G06T 7/0012; G16H 10/40; G16H 30/20; G16H 30/40; H04N 5/2256; H04N 5/23299
USPC ......................................................... 348/143
See application file for complete search history.

(56) References Cited

U.S. PATENT DOCUMENTS

| | | | |
|---|---|---|---|
| 2004/0241832 A1 | 12/2004 | Muraki et al. | |
| 2008/0131922 A1 | 6/2008 | Muraki et al. | |
| 2010/0092031 A1* | 4/2010 | Bergeron | G06K 9/2018 |
| | | | 382/103 |
| 2011/0092762 A1 | 4/2011 | Wong et al. | |
| 2011/0105834 A1 | 5/2011 | Wong et al. | |
| 2015/0204773 A1* | 7/2015 | Ozcan | G01N 15/1463 |
| | | | 382/103 |
| 2016/0050374 A1* | 2/2016 | Shabtay | H04N 5/225 |
| | | | 348/240.3 |
| 2016/0245813 A1* | 8/2016 | Mir | B01L 3/5085 |
| 2017/0166948 A1* | 6/2017 | Matsumoto | C12Q 1/02 |
| 2017/0283754 A1* | 10/2017 | Petersen | C12M 21/06 |
| 2017/0342367 A1* | 11/2017 | Figg | C12M 47/04 |
| 2019/0026536 A1* | 1/2019 | Matsubara | H04N 5/2353 |
| 2019/0212537 A1 | 7/2019 | Ohashi et al. | |
| 2019/0220979 A1 | 7/2019 | Aoki et al. | |
| 2019/0331905 A1 | 10/2019 | Shinoda et al. | |
| 2020/0158719 A1* | 5/2020 | Akiyoshi | G01N 21/6428 |

FOREIGN PATENT DOCUMENTS

| | | |
|---|---|---|
| EP | 3473998 A1 | 4/2019 |
| EP | 3480291 A1 | 5/2019 |
| JP | 2005-027623 A | 2/2005 |
| JP | 2011-192109 A | 9/2011 |
| JP | 2013-502233 A1 | 1/2013 |
| WO | WO 2011/025736 A1 | 3/2011 |
| WO | WO 2012/115153 A1 | 8/2012 |
| WO | WO 2016/039010 A1 | 3/2016 |
| WO | WO 2016/050964 A1 | 4/2016 |
| WO | WO 2018025766 A1 | 2/2018 |

OTHER PUBLICATIONS

International Preliminary Report on Patentability and English translation thereof dated Jun. 13, 2019 in connection with International Application No. PCT/JP2017/037848.

Extended European Search Report dated Nov. 18, 2019 in connection with European Application No. 17875094.9.

Haupt et al., Automated selection and harvesting of pluripotent stem cell colonies, Biotechnology and Aplied Biochemistry, Mar. 1, 2012, vol. 59, No. 2, pp. 77-87.

Marx et al., Automatic Production of Induced Pluripotent Stem Cells, Procedia CIRP 5, Jan. 1, 2013, vol. 5, pp. 2-6.

* cited by examiner

INFORMATION PROCESSING APPARATUS, INFORMATION PROCESSING METHOD, PROGRAM, AND OBSERVATION SYSTEM FOR CELL IMAGE CAPTURE

CROSS-REFERENCE TO RELATED APPLICATIONS

This application claims the benefit under 35 U.S.C. § 371 as a U.S. National Stage Entry of International Application No. PCT/JP2017/037848, filed in the Japanese Patent Office as a Receiving Office on Oct. 19, 2017, which claims priority to Japanese Patent Application Number JP2016-231818, filed in the Japanese Patent Office on Nov. 29, 2016, each of which is hereby incorporated by reference in its entirety.

TECHNICAL FIELD

The present technology relates to an information processing apparatus, an information processing method, a program, and an observation system applicable to capture images of cells.

BACKGROUND ART

In recent years, cultured fertile ova are often transplanted to livestock in a domestic livestock industry. However, for doing this, it is desirable to provide a technique for culturing a large amount of fertile ova. For example, Patent Literature 1 discloses a technique that fertile ova of livestock, etc. are cultured and are grown to a transplantable state.

CITATION LIST

Patent Literature

Patent Literature 1: Japanese Patent Application Laid-open No. 2011-192109

DISCLOSURE OF INVENTION

Technical Problem

In order to grow fertile ova to a transplantable state, it needs to regularly check quality of the fertile ova. Specifically, it needs to regularly image-capture the fertile ova for each glowing stage and to observe a growing state of the fertile ova. At this time, it is desirable to provide a technique for efficiently capturing images of growing fertile ova by keeping stress as low as possible.

The present technology is made in view of the above-mentioned circumstances, and it is an object of the present technology to provide an information processing apparatus, an information processing method, a program, and an observation system with which images of cells under observation are efficiently captured.

Solution to Problem

In order to achieve the object, an information processing apparatus according to an embodiment of the present technology includes an image-capture controller unit, an image-capture area classifier unit, and an observation controller unit.

The image-capture controller unit controls an image-capture mechanism to capture images of a culture vessel including a plurality of wells that house cells for each image-capture area.

The image-capture area classifier unit applies image processing to the images captured by the image-capture mechanism and classifies the plurality of image-capture areas into a first image-capture area of which image-capturing is continued and a second image-capture area of which image-capturing is not continued on the basis of a result of the image processing.

The observation controller unit instructs the image-capture controller unit to capture an image of an image-capture area classified as the first image-capture area and not to capture an image of an image-capture area as the second image-capture area.

With this configuration, since the image-capture controller unit controls the image-capture mechanism on the basis of the instruction by the observation controller unit, capturing the images of the second image-capture area is omitted. Thus, it is possible to shorten the time to capture the images of the cells under observation and to effectively capture the images of the cells.

The image-capture area classifier unit may include an evaluating unit that evaluates whether or not each of the plurality of wells included in each of the image-capture area is suitable for observation, and a determining unit that determines the image-capture area as the first image-capture area or the second image-capture area on the basis of an evaluation result of the evaluating unit.

With this configuration, it can be determined whether or not capturing images of the image-capture areas is continued on the basis of each state of the plurality of wells.

The determining unit may determine the image-capture area as the second image-capture area in a case where all wells included in the image-capture area are unsuitable for observation and may determine the image-capture area as the first image-capture area in a case where at least one well included in the image-capture area is suitable for observation.

With this configuration, it prevents fertile ova under observation from uncapturing.

The evaluating unit may evaluate whether or not the wells are suitable for observation in accordance with a growing state of the cells housed in the wells.

With this configuration, it can be determined whether or not capturing images of the image-capture areas is continued on the basis of each state of the plurality of wells.

The evaluating unit may evaluate the growing state of the cells in accordance with machine learning algorithm.

With this configuration, the growing state of the cells can be evaluated with a high degree of accuracy.

The evaluating unit may evaluate the wells each of which houses one cell as the wells suitable for observation and the wells that house the plurality of cells and the wells that house no cells as the wells unsuitable for observation.

The observation controller unit may instruct the image-capture controller unit such that the number of times of capturing the images of a specific first image-capture area included in the plurality of image-capture areas classified as the first image-capture area is greater than the number of times of capturing the images of a first image-capture area other than the specific first image-capture area.

With this configuration, as compared with the case that the images of all the fertile ova housed in the culture vessel are captured, the images of the fertile ova of highly interest can be intensively captured, and the images of the fertile ova can be highly selectively captured.

The image-capture controller unit may change a first moving route along which the image-capture mechanism passes through all the plurality of image-capture areas to a second moving route shorter than the first moving route on the basis of an instruction by the observation controller unit.

With this configuration, the moving route of the image-capture mechanism is optimized, and it is possible to shorten the time to capture the images of the fertile ova under observation.

In order to achieve the object, in an information processing method according to an embodiment of the present technology, an image-capture mechanism is controlled to capture images of a culture vessel including a plurality of wells that house cells for each image-capture area.

Image processing is applied to the images captured by the image-capture mechanism, the plurality of image-capture areas are classified into a first image-capture area of which image-capturing is continued and a second image-capture area of which image-capturing is not continued on the basis of a result of the image processing.

The image-capture controller unit is instructed to capture an image of an image-capture area classified as the first image-capture area and not to capture an image of an image-capture area as the second image-capture area.

In order to achieve the object, a program according to an embodiment of the present technology causes the image processing apparatus to execute the following steps:

A step of controlling an image-capture mechanism to capture images of a culture vessel including a plurality of wells that house cells for each image-capture area.

A step of applying image processing to the images captured by the image-capture mechanism and classifying the plurality of image-capture areas into a first image-capture area of which image-capturing is continued and a second image-capture area of which image-capturing is not continued on the basis of a result of the image processing.

A step of instructing the image-capture controller unit to capture an image of an image-capture area classified as the first image-capture area and not to capture an image of an image-capture area as the second image-capture area.

In order to achieve the object, an observation system according to an embodiment of the present technology includes a culture vessel, an image-capture mechanism, a light source, and an information processing apparatus.

The culture vessel includes a plurality of wells that house cells.

The image-capture mechanism captures images of the culture vessel for each image-capture area.

The light source irradiates the culture vessel with light.

The information processing apparatus includes an image-capture controller unit, an image-capture area classifier unit, and an observation controller unit.

The image-capture controller unit controls the image-capture mechanism.

The image-capture area classifier unit applies image processing to the images captured by the image-capture mechanism and classifies the plurality of image-capture areas into a first image-capture area of which image-capturing is continued and a second image-capture area of which image-capturing is not continued on the basis of a result of the image processing.

The observation controller unit instructs the image-capture controller unit to capture an image of an image-capture area classified as the first image-capture area and not to capture an image of an image-capture area as the second image-capture area.

The observation system may further include a light shielding filter that shields light such that only a field-of-view range of the image-capture mechanism is irradiated with the light from the light source at a time of capturing the images of the first image-capture area by the image-capture mechanism.

With this configuration, since the fertile ova in the image-capture areas other than the first image-capture area are not irradiated with light, when the image-capture mechanism captures the images of the first image-capture area. Thus, photo-damages (phototoxicity) to the fertile ova are reduced. Note that the photo-damages (phototoxicity) include photo-damages, thermal damages, and other damages to DNA and chromosomes affected by light.

The light source may be an illumination device configured to be capable of locally irradiating each of the plurality of image-capture areas with light, the illumination device irradiating only the field-of-view range of the image-capture mechanism with light at a time of capturing the images of the first image-capture area by the image-capture mechanism.

With this configuration, since the fertile ova in the image-capture areas other than the first image-capture area are not irradiated with light, when the image-capture mechanism captures the images of the first image-capture area. Thus, photo-damages (phototoxicity) to the fertile ova are reduced. Note that the photo-damages (phototoxicity) include photo-damages, thermal damages, and other damages to DNA and chromosomes affected by light.

The culture vessel may include a cell removal mechanism configured to be capable of removing cells housed in the wells included in the image-capture area classified as the second image-capture area.

With this configuration, a negative influence of the cells on the cells housed in the wells of the first image-capture areas can be suppressed.

Advantageous Effects of Invention

An information processing apparatus, an information processing method, a program, and an observation system with which images of cells under observation can be efficiently captured can be provided.

MODE(S) FOR CARRYING OUT THE INVENTION

Figure 1:
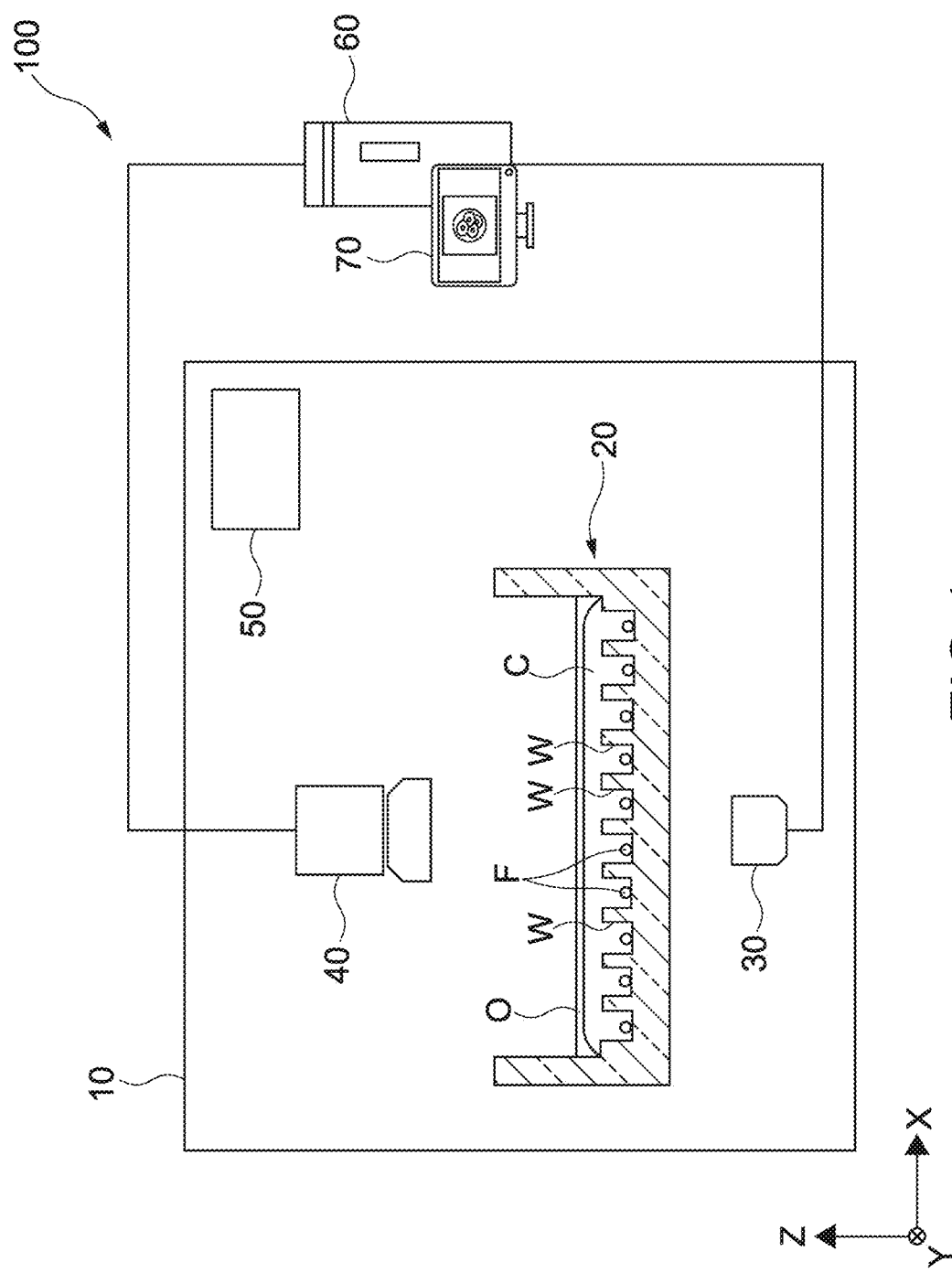
FIG. 1 is a diagram schematically showing a configuration example of an observation system according to a first embodiment of the present technology.

Hereinafter, embodiments of the present technology will be described with reference to the drawings.

In the drawings, perpendicular X axis, Y axis, and Z axis are shown as necessary. The X axis, the Y axis, and the Z axis are common in all the drawings.

First Embodiment

Configuration of Observation System

FIG. 1 is a diagram schematically showing a configuration example of an observation system 100 according to a first embodiment of the present technology. As shown in FIG. 1, the observation system 100 includes a culturing device 10, a culture vessel 20, a light source 30, an image-capture mechanism 40, a gas controller unit 50, an information processing apparatus 60, and display device 70.

As shown in FIG. 1, the culturing device 10 is a chamber, in which the culture vessel 20 (dish), the light source 30, image-capture mechanism 40, and the gas controller unit 50 are housed. The culture vessel 20 includes a plurality of wells W, as shown in FIG. 1. Each well W is configured to be capable of housing one cell, here, a fertile ovum F. In addition, the wells W are arrayed in a matrix in the culture vessel 20 (see FIG. 4). Further, the culturing device 10 is configured to allow arbitrary gas to flow into the culturing device 10.

Note that, the "cell" conceptually includes at least a single cell and an aggregate of a plurality of cells in this specification. The "cell" has any three-dimensional shape as an example and includes at least unfertilized egg cells (ova), fertile ova, and embryos. In the present technology, as the cells housed in the culture vessel 20, fertile ova are illustrated for explanation. In addition, the cells may be cells derived from livestock such as cows and pigs or may be cells of a human or the like.

Culture liquid C and oil O are injected into the culture vessel 20 in addition to the wells W. The oil O coats the culture liquid C and has a function to inhibit evaporation of the culture liquid C.

The material of the culture vessel 20 is not particularly limited. The culture vessel 20 is made from, for example, an inorganic material such as metal, glass, and silicon, or made from an organic material such as polystyrene resin, polyethylene resin, polypropylene resin, ABS resin, nylon, acrylic resin, fluororesin, polycarbonate resin, polyurethane resin, methylpentene resin, phenol resin, melamine resin, epoxy resin, and vinyl chloride resin, and typically made from polystyrene resin.

When the image-capture mechanism 40 captures images of the fertile ova F in the culture vessel 20, the light source 30 irradiates light. The light source 30 is an LED (Light Emitting Diode) that irradiates light having a certain wavelength, e.g., a red LED that irradiates light having a wavelength of 640 nm or the like.

The image-capture mechanism 40 is configured to be capable of capturing the fertile ova F housed in the culture vessel 20 and obtaining the images of the fertile ova F. The image-capture mechanism 40 includes a lens barrel, a solid state image sensor, a drive circuit that drives them, and the like. The lens barrel includes a group of lenses capable of moving in a light-axis direction (Z-axis direction). The solid state image sensor captures light from an object passing through the lens barrel, and is a CMOS (Complementary Metal Oxide Semiconductor), a CCD (Charge Coupled Device), or the like.

The image-capture mechanism 40 is configured to be capable of moving in the light-axis direction (Z-axis direction) and the horizontal direction (XY plane direction). The image-capture mechanism 40 captures the images of the fertile ova F held in the culture vessel 20 while moving in the XY plane direction. Further, the image-capture mechanism 40 may be configured to be capable of capturing not only still images but also motion images.

The image-capture mechanism 40 of the present embodiment is a visible camera. Not limited to this, the image-capture mechanism 40 may be an infrared (IR) camera, a polarization camera, or the like.

The gas controller unit 50 is configured to control the temperature and the humidity of gas in the culturing device 10 to thereby make the environment appropriate to growing of the fertile ova F. The gas controller unit 50 of the present embodiment is capable of controlling the temperature of the culturing device 10 at about 38° C., for example. Note that the kind of the gas introduced into the culturing device 10 is not specifically limited and is typically nitrogen, oxygen, carbon dioxide, or the like.

The information processing apparatus 60 includes hardware necessary for a computer such as a CPU (Central Processing Unit), a ROM (Read Only Memory), a RAM (Random Access Memory), and an HDD (Hard Disk Drive). In the present embodiment, for example, the image processing apparatus 60 is a PC (Personal Computer) or the like, but the image processing apparatus 60 may be an arbitrary computer other than a PC.

When the CPU loads a program of the present technology stored in the ROM or the HDD in the RAM and executes the program, the CPU controls operations of the respective blocks (described later) of the image processing apparatus 60. In the present embodiment, the information processing apparatus 60 controls operations of the image-capture mechanism 40 and light emission of the light source 30 and captures the images of the plurality of fertile ova F.

The program is installed in the image processing apparatus 60 via a variety of recording media (internal memories), for example. Alternatively, the program may be installed via the Internet or the like.

The display device 70 is configured to be capable of displaying the images and the like captured by the image-capture mechanism 40. Further, the display device 70 may be a touch panel including a display device and an operation device integrally formed, or the like.

Figure 2:
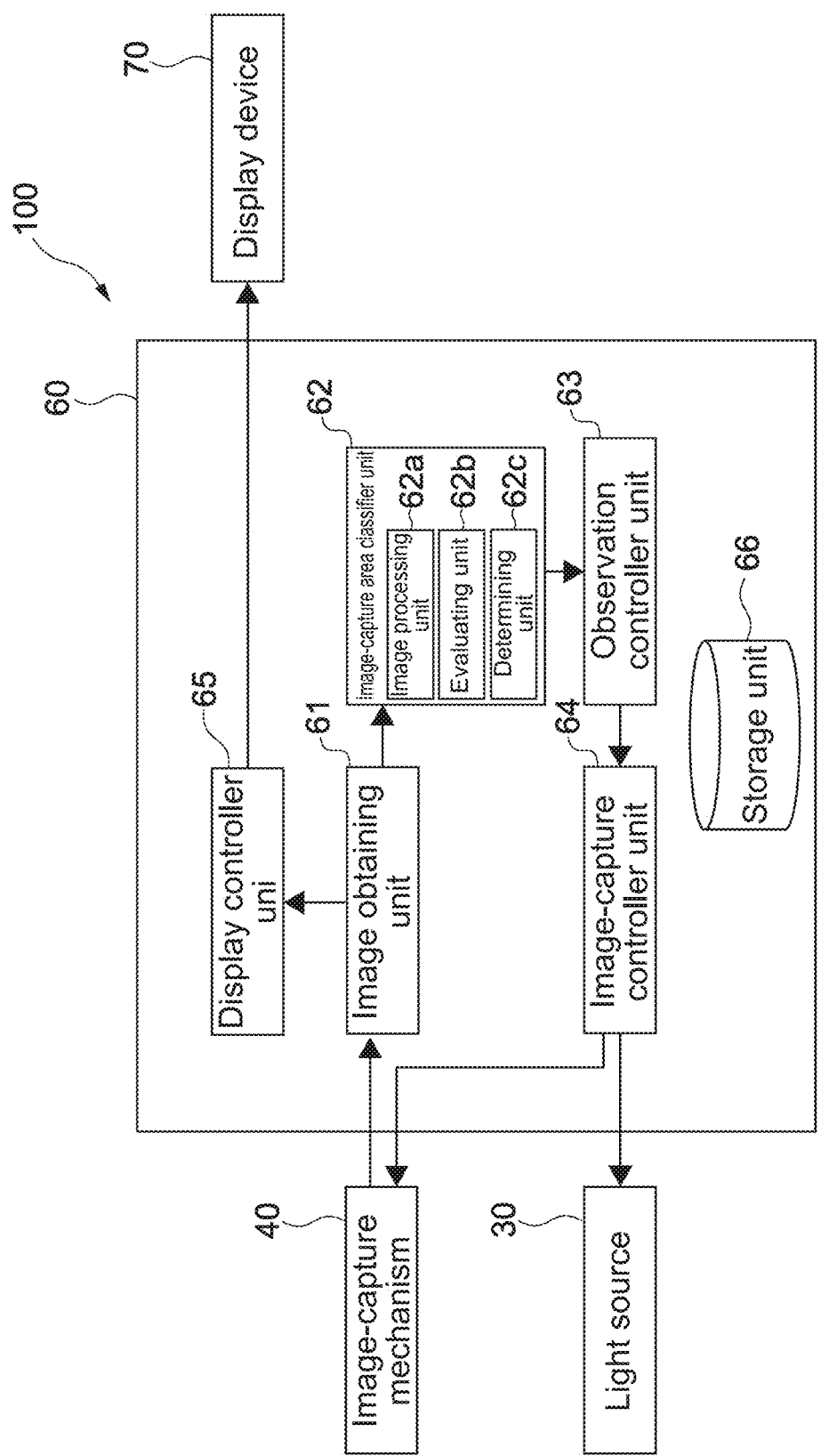
FIG. 2 is a function block diagram of the observation system.

Next, a configuration of the image processing apparatus 60 will be described. FIG. 2 is a function block diagram of the observation system 100.

As shown in FIG. 2, the image processing apparatus 60 includes an image obtaining unit 61, an image-capture area classifier unit 62, an observation controller unit 63, an image-capture controller unit 64, a display controller unit 65, and a storage unit 66.

The image obtaining unit 61 obtains the images captured by the image-capture mechanism 40 from the image-capture mechanism 40 or the storage unit 66 and outputs the obtained images to the image-capture area classifier unit 62 and the display controller unit 65.

The image-capture area classifier unit 62 includes an image processing unit 62a, an evaluating unit 63b and a determining unit 62c. The image processing unit 62a applies predetermined image processing to the images obtained from the image obtaining unit 61. An evaluating unit 62b evaluates a state of an object to be image-captured on the basis of the result of the image processing by the image processing unit 62a. The determining unit 62c determines whether or not the object to be image-captured is included in a field-of-view range of the image-capture mechanism 40 on the basis of an evaluation result of the evaluating unit 62b.

The observation controller unit 63 controls the image-capture controller unit 64 on the basis of a determination result of the determining unit 62c. The image-capture controller unit 64 controls an operation of the image-capture mechanism 40 and a timing of the light emission of the light source 30. The image-capture controller unit 64 of the present embodiment can control the operation of the image-capture mechanism 40 such that the object to be image-captured is captured for each field-of-view range of the image-capture mechanism 40.

The display controller unit 65 outputs the image obtained from the image obtaining unit 61 to the display device 70. The storage unit 66 stores the images or the like obtained by the image obtaining unit 61.

Image Obtaining Method

Figure 3:
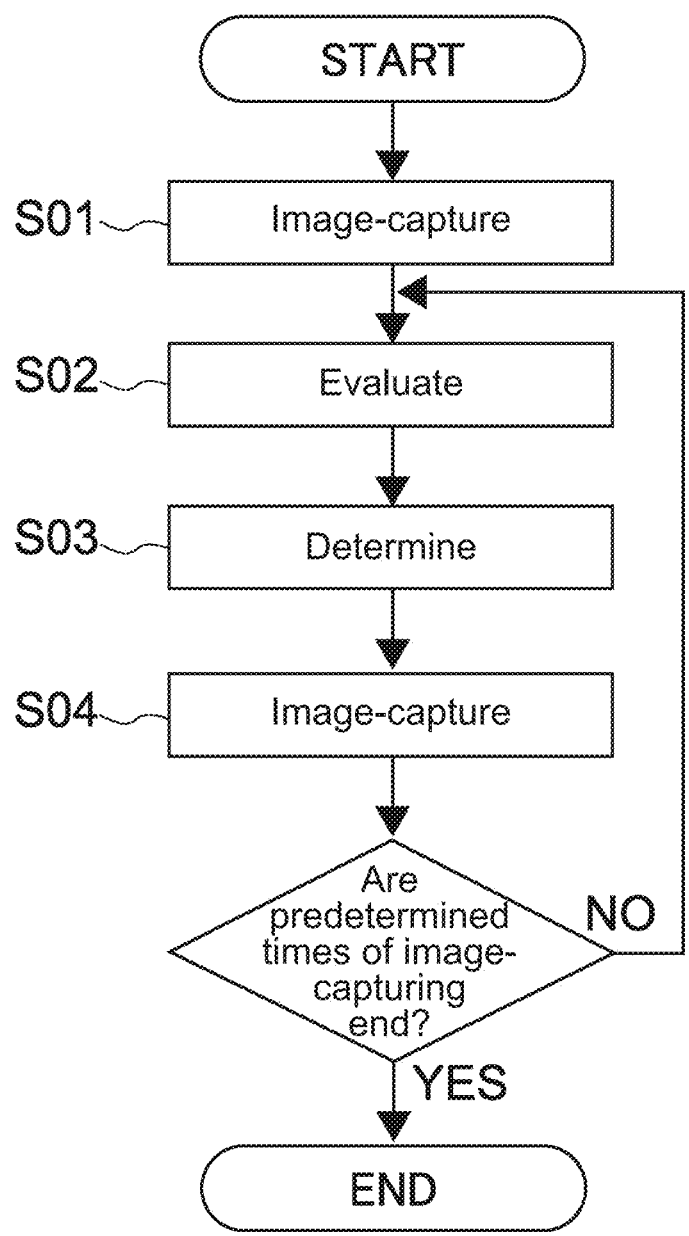
FIG. 3 is a flowchart showing a method of obtaining images by the observation system.

FIG. 3 is a flowchart showing a method of obtaining images by the observation system 100. Hereinafter, the method of obtaining the images by the observation system 100 will be described with reference to FIG. 3, as appropriate.

Step S01: Image-Capture

Figure 4:
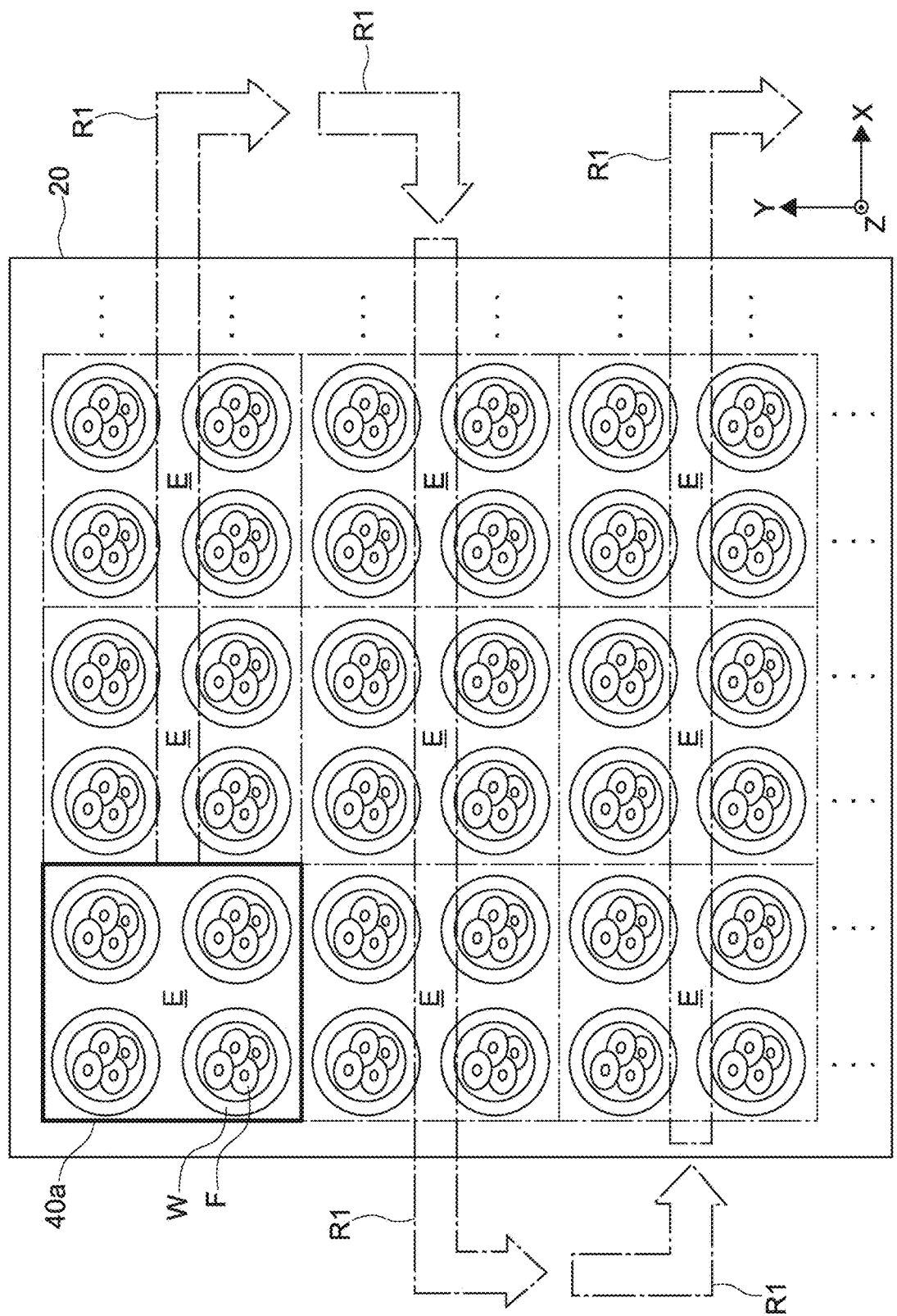
FIG. 4 is a diagram schematically showing a moving route of an image-capture mechanism of the observation system.

In Step S01, images of the culture vessel 20 are captured for each image-capture area E and images of all the fertile ova F housed in the plurality of wells W arrayed in the culture vessel 20 are captured. FIG. 4 schematically shows a moving route of the image-capture mechanism 40 in Step S01 and shows a state that the image-capture mechanism 40 captures the images of the fertile ova F. Note that each image-capture area E is an imaginary area set on the culture vessel 20 corresponding to a field-of-view range 40a of the image-capture mechanism 40.

First, the light source 30 irradiates light from below of the culture vessel 20. This allows the culture vessel 20 to be irradiated with the light from the light source 30. Next, the image-capture mechanism 40 captures the images of the fertile ova F housed in the wells W within the field-of-view range 40a (image-capture area E) of the image-capture mechanism 40.

Next, the image-capture controller unit 64 causes the image-capture mechanism 40 to be moved in the X direction. Then, the field-of-view range 40a of the image-capture mechanism 40 moves toward the image-capture area E adjacent to the image-capture area E in which the image-capture is completed. Similar to as described above, the images of the fertile ova F housed in the wells W are captured.

Thereafter, by controlling the image-capture mechanism 40 by the image-capture controller unit 64, images of the fertile ova F housed in the wells W are captured for each image-capture area E while the image-capture mechanism 40 follows a moving route R1 set in advance, as shown in FIG. 4. Thus, the images of all the fertile ova F housed in the plurality of wells W arrayed in the culture vessel 20 are captured. The images of the plurality of fertile ova F captured for each image-capture area E are stored in the storage unit 66.

Note that the field-of-view range 40a (image-capture area E) of the image-capture mechanism 40 is a range that four wells W are housed as shown in FIG. 4. Not limited to this, it is possible to be arbitrarily set. For example, the field-of-view range 40a (image-capture area E) may a range in which only one well W is housed, or two or more wells W are housed.

Step S02: Evaluate

In Step S02, the image-capture mechanism 40 applies the image processing to the plurality of images captured for each image-capture area E. Then, it evaluates whether or not each of the plurality of wells included in the respective image-capture areas E is suitable for observation.

Firstly, the image obtaining unit 61 outputs the images of the plurality of fertile ova F captured for each image-capture area E to the image processing unit 62a. The image processing unit 62a applies the image processing to the images of the plurality of fertile ova F obtained from the image obtaining unit 61.

Specifically, the image processing unit 62a executes processing of extracting profiles of the plurality of fertile ova F obtained from the image obtaining unit 61, for example. Any known technique is applicable to this processing, An example of the processing of extracting the profiles includes thresholding processing of the images of the fertile ova F.

Next, the image processing unit 62a outputs the images of the plurality of fertile ova F after the image processing to the evaluating unit 62b. The evaluating unit 62b evaluates whether or not each of the plurality of wells W included in the respective image-capture areas E is suitable for observation on the basis of the result of the image processing of the image processing unit 62a.

Specifically, the evaluating unit 62b analyzes the images of the fertile ova F after the image processing and calculates evaluation values about growing of the fertile ova F in accordance with machine learning algorithm. Then, the evaluating unit 62b evaluates a growing state of the fertile ova F for each well W on the basis of the evaluation values and evaluates whether or not the respective wells W are suitable for observation in accordance with the evaluation result.

The evaluating unit 62b of the present embodiment can evaluate the growing state of the fertile ova F with a high degree of accuracy by evaluating the growing state of the cells housed in the wells W in accordance with the machine learning algorithm.

The machine learning algorithm used for evaluating the growing of the fertile ova F by the evaluating unit 63a is not particularly limited. For example, a machine learning algorithm that employs a neural network such as RNN (Recurrent Neural Network), CNN (Convolutional Neural Network), and MLP (Multilayer Perceptron) may be used. Alternatively, an arbitrary machine learning algorithm that executes supervised learning, unsupervised learning, semi-supervised learning, reinforcement learning, or other learning may be used.

Further, criteria of evaluating the growing of the fertile ova F by the evaluating unit 62b is also not especially limited and may be arbitrarily set. For example, the evaluating unit 62b can evaluate the growing of the fertile ova F by criteria including size, shape, sphericity, permeability, cleavage number (rate), uniformity of cleavage, symmetric property, amount or rate of fragmentation, or the like of the fertile ova F.

Step S03: Determine

In Step S03, the determining unit 62c determines each of the plurality of image-capture areas E as the first image-capture areas E1 or the second image-capture areas E2 on the basis of the evaluation results of the evaluating unit 62b.

The first image-capture areas E1 are the image-capture areas E including at least one well W evaluated as suitable for observation by the evaluating unit 62b in the former Step S02. The image-capture areas E determined as the first image-capture areas E1 by the determining unit 62c are included again in the field-of-view range 40a of the image-capture mechanism 40 in the latter Step S04.

Here, as described above, in a case where at least one well W included in the image-capture area E is suitable for observation, as the determining unit 62c determines the image-capture areas E as the first image-capture areas E1, it prevents the fertile ova F under observation from uncapturing.

The second image-capture areas E2 are the image-capture areas E including only the wells W evaluated as unsuitable for observation by the evaluating unit 62b in the former Step S02. All the wells W included in the second image-capture areas E2 house the fertile ova F that are evaluated as undergrown by the evaluating unit 62b in accordance with the predetermined machine learning algorithm. The image-capture areas E determined as the second image-capture areas E2 by the determining unit 62c are not included in the field-of-view range 40a of the image-capture mechanism 40 in the latter Step S04.

Step S04: Image-Capture

Figure 5:
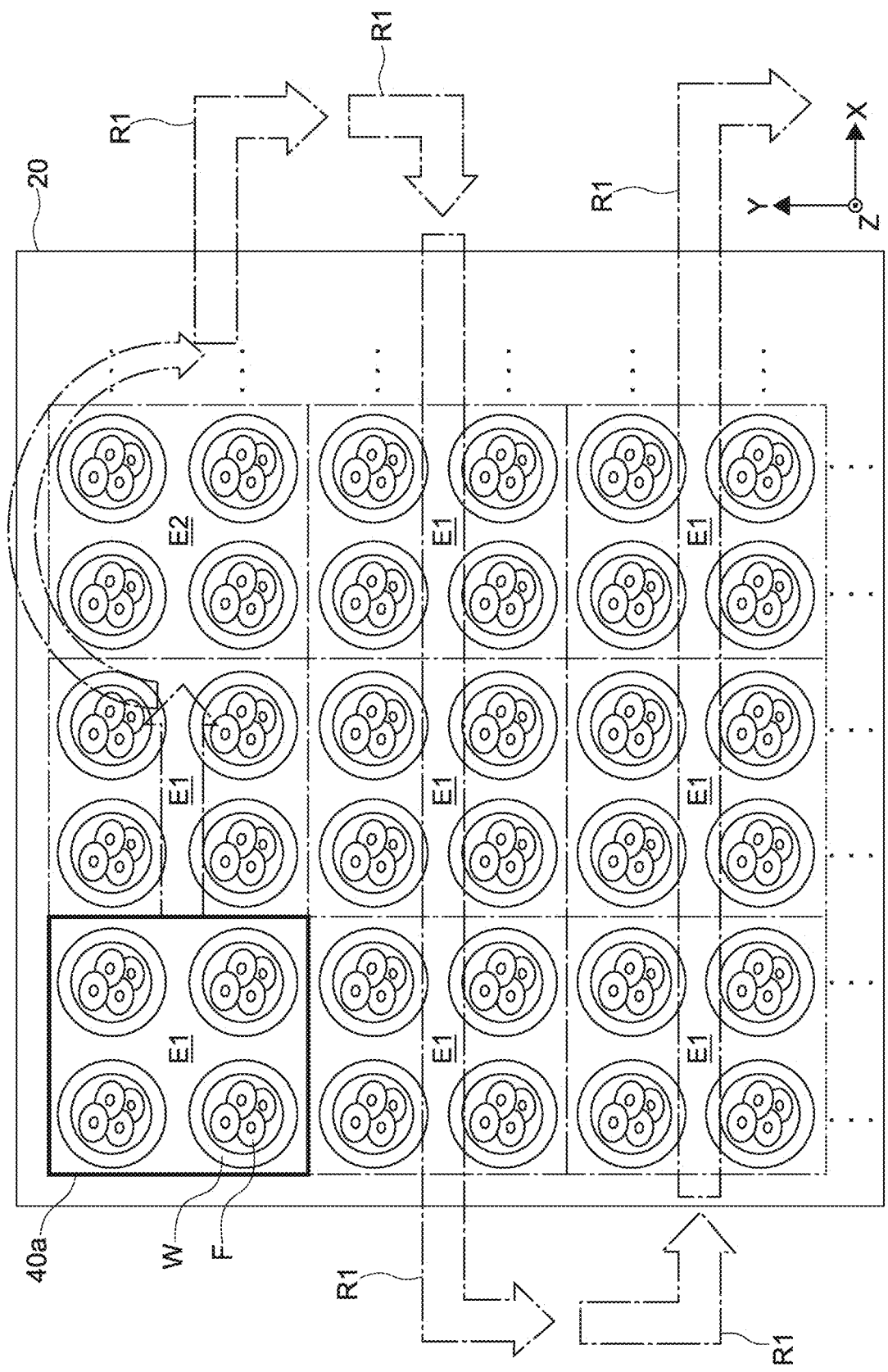
FIG. 5 is a diagram schematically showing a moving route of an image-capture mechanism of the observation system.

In Step S04, among the plurality of image-capture areas E included in the culture vessel 20, the image-capture mechanism 40 captures the images only in the image-capture areas E classified as the first image-capture areas E1 in the former Step S03. FIG. 5 schematically shows the moving route of the image-capture mechanism 40 in Step S04 and shows a state that the image-capture mechanism 40 captures the images of the fertile ova F.

First, the observation controller unit 63 instruct the image-capture controller unit 64 to capture the images of the image-capture areas E classified as the first image-capture areas E1 and not to capture the images of the image-capture areas E classified as the second image-capture areas E2 on the basis of the determination result of the determining unit 62c.

Next, the image-capture areas E classified as the first image-capture areas E1 in the former Step S03 are included in the field-of-view range 40a of the image-capture mechanism 40. Next, similar to Step S01, the image-capture mechanism 40 captures the images of the fertile ova F housed in the wells W in the first image-capture areas E1.

Here, in a case where the image-capture area E adjacent to the first image-capture area E1 is another first image-capture area E1, the image-capture controller unit 64 causes the field-of-view range 40a to move from the image-captured first image-capture area E1 to a next first image-capture area E1. Then, similar to as described above, the images of the fertile ova F housed in the wells W are captured.

On the other hand, in a case where the image-capture area E adjacent to the first image-capture areas E1 is the second image-capture area E2, the image-capture controller unit 64 causes the field-of-view range 40a not to move to the second image-capture area E2 but to the first image-capture area E1 adjacent to second image-capture area E2 on the basis of an instruction by the observation controller unit 63 as shown in FIG. 5. Then, similar to as described above, the images of the fertile ova F housed in the wells W are captured.

Hereinafter, the image-capture controller unit 64 controls the image-capture mechanism 40 on the basis of the instruction by the observation controller unit 63, and the image-capture mechanism 40 thus captures the images of all the fertile ova F housed in the wells W in the first image-capture area E1 along the moving route R1 set in advance, as shown in FIG. 5. The images of the plurality of fertile ova F captured for each first image-capture area E1 are stored in the storage unit 66.

Specifically, in Step S04, since the image-capture controller unit 64 controls the image-capture mechanism 40 on the basis of the instruction by the observation controller unit 63, capturing the images of the second image-capture area E2 is omitted and the image-capture mechanism 40 captures the images of only the first image-capture area E1.

Thus, it is possible to shorten the time to capture the images of the fertile ova F under observation and to effectively capture the images of the fertile ova F. Further, since the images of the fertile ova F in the second image-capture areas E2 are not captured, the total time period, in which the fertile ova F under observation are irradiated with light from the light source 30, is shortened, and photo-damages (phototoxicity) to the fertile ova F are reduced. Note that the photo-damages (phototoxicity) include photo-damages, thermal damages, and other damages to DNA and chromosomes affected by light. Also in the description later, the same meaning is applied.

In the present embodiment, as shown in FIG. 3, a series of cycles in Step S02 to S04 is repeated for predetermined times. In this way, a plurality of cycles to capture the images over an entire area of the culture vessel 20 for each image-capture area E is repeated, and the images of the fertile ova F in the respective image-capture areas E are captured in a plurality of times.

Here, in the process of repeating the series of cycles in Step S02 to S04, in the image-capture areas E determined as the first image-capture areas E1, the images are continuously captured by the image-capture mechanism 40, and in the image-capture areas E determined as the second image-capture areas E2, the images are not continuously captured and the image-capture is ended.

Further, in the observation system 100 of the present embodiment, the series of cycles in Step S02 to S04 are repeated for an arbitrary time, for example, for a predetermined duration, e.g., at an interval of 15 minutes or one day. Thus, a progress of the growing of the fertile ova F can be observed for each image-capture area E. Note that the observation system 100 may obtain the images in real time as necessary or may cause the display device 70 to display the state of the fertile ova F for observation whenever necessary.

Modification Example

The image obtaining method by the observation system 100 is not limited to the above-described method, and modification, addition, or the like may be performed, as appropriate.

In the above-described Step S02, the evaluating unit 62b evaluates the growing state of each of the fertile ova F housed in the plurality of wells W in the image-capture areas E, but it is not limited to this.

For example, in Step S02, the evaluating unit 62b may evaluate whether or not the fertile ova F are housed in the plurality of wells W in the image-capture areas E. In this case, the wells W that do not house the fertile ova F may be evaluated as unsuitable for observation.

Since the image-capture areas E including only the wells W that do not house the fertile ova F are thus determined as the second image-capture areas E2, capturing the images of the image-capture areas E including only the wells W that do not house the fertile ova F is omitted. As a result, image-capture efficiency is improved when the images of the plurality of wells W arrayed in the culture vessel 20 are captured for each image-capture area E.

Further, in Step S02, the evaluating unit 62b may evaluate the number of the fertile ova F housed in the plurality of wells W. In this case, the wells each of which houses one cell may be evaluated as the wells suitable for observation and the wells that house the plurality of cells may be as the wells unsuitable for observation.

Specifically, the image-capture areas E including only the wells W that house the plurality of cells are determines as the second image-capture areas E2 and capturing the images of the image-capture areas E may be omitted. When the evaluating unit 62b evaluates the growing state of the fertile ova F in accordance with the machine learning algorithm, the wells W house the plurality of fertile ova F. As a result, it inhibits to appropriately learn the growing state of the fertile ova F by the evaluating unit 62b.

Further, the image-capture areas E determined as the second image-capture areas E2 are not limited to the image-capture areas E. For example, the image-capture areas E including only the wells E evaluated as well grown by the evaluating unit 62b in accordance with the predetermined machine learning algorithm may also be determined as the second image-capture areas E2. As a result, the number of times to irradiate well grown fertile ova F with light from the light source 30 is decreased and the photo-damages (phototoxicity) to the fertile ova F are reduced.

Further, the image-capture areas E including only the wells W that house the fertile ova F evaluated as undergrown and the wells W that houses no fertile ova F, the image-capture areas E including only the wells W that house the fertile ova F evaluated as undergrown and the wells W that house the plurality of fertile ova F, and the image-capture areas E including only the wells W that houses no fertile ova F and the wells W that house the plurality of fertile ova F may also be determined as the second image-capture area E2.

In addition, the image-capture areas E including only the wells W that house the fertile ova F evaluated as well grown and the wells W that house no fertile ova F and the image-capture areas E including only the wells W that houses the fertile ova F evaluated as well grown and the wells W that house the plurality of fertile ova F may also be determined as the second image-capture area E2.

Figure 6:
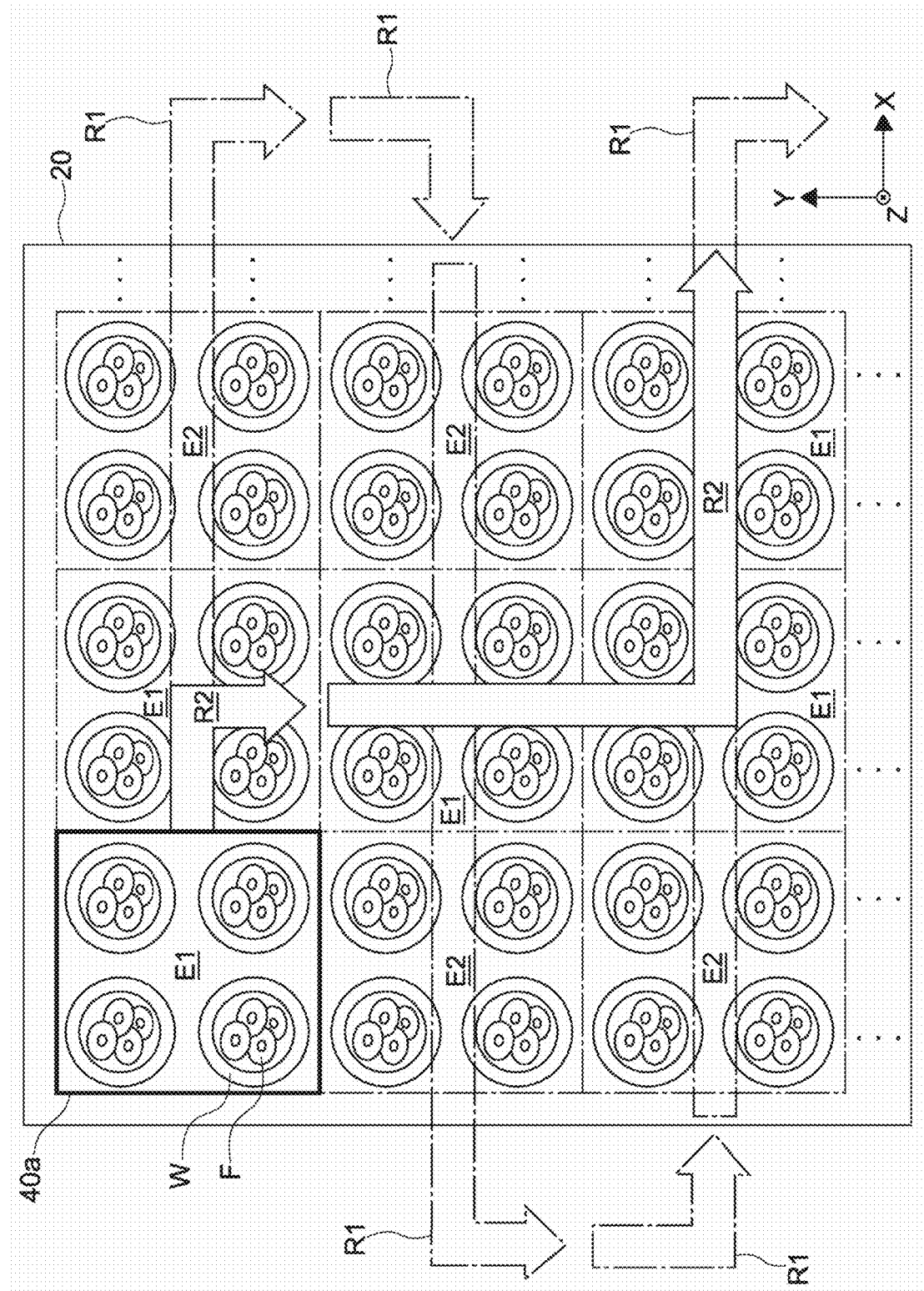
FIG. 6 is a diagram schematically showing a moving route of an image-capture mechanism according to a modification example of the first embodiment.

Further, in the image obtaining method, the moving route R1 of the image-capture mechanism 40 may be changed. FIG. 6 schematically shows the moving route of the image-capture mechanism 40 according to a modification example of the first embodiment. Note that arrows shown by alternate long and short dash lines represent the moving route of the image-capture mechanism 40 before changing and arrow shown by solid lines represent the moving route of the image-capture mechanism 40 after changing.

The image-capture controller unit 64 may change the moving route R1 along which the image-capture mechanism 40 passes through all the plurality of image-capture areas E to a second moving route R2 shorter than the first moving route R1 on the basis of an instruction by the observation controller unit 63 in Step S04.

In this manner, the moving route R1 set in advance is optimized to moving route R2 that successfully passes through the first image-capture areas E1 as shown in FIG. 6 and the images of the first image-capture areas E1 can be efficiently captured. Accordingly, it is possible to shorten the time to capture the images of the fertile ova F under observation.

Note that, the moving route R2 shown in FIG. 6 passes through only the first image-capture area E1. Not limited to this, the moving route R2 may pass through the second image-capture areas E2 as necessary as long as the image-capture mechanism 40 passes through all the first image-capture areas E1 set on the culture vessel 20 and the moving route R2 is shorter than the moving route R1.

Second Embodiment

Figure 7:
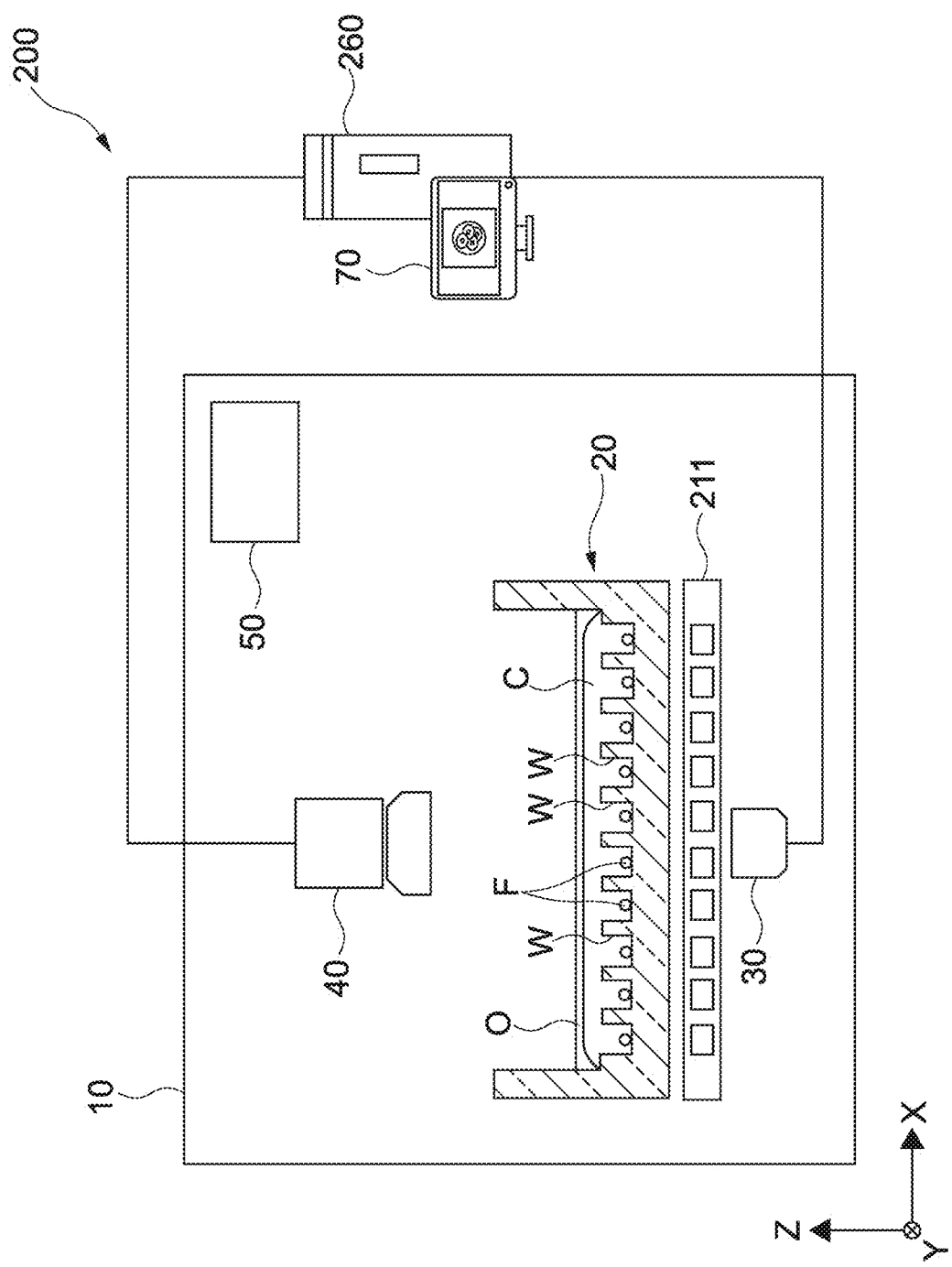
FIG. 7 is a diagram schematically showing a configuration example of an observation system according to a second embodiment of the present technology.

Next, an observation system 200 according to a second embodiment of the present technology will be described. FIG. 7 schematically shows a configuration example of the observation system 200 according to a second embodiment of the present technology. Hereinafter, configuration similar to the configuration of the first embodiment will be denoted by similar reference signs, and detailed description thereof will be omitted.

Configuration of Observation System

As shown in FIG. 7, the observation system 200 of the second embodiment includes the culturing device 10, the culture vessel 20, the light source 30, the image-capture mechanism 40, the gas controller unit 50, a light shielding filter 211, an information processing apparatus 260 and the display device 70.

As shown in FIG. 7, the light shielding filter 211 is arranged between the light source 30 and the culture vessel 20. The light shielding filter 211 can be, for example, a liquid crystal filter and is configured to be capable of switching transmission and shielding of light from the light source 30 for each image-capture area E.

The light shielding filter 211 according to the present embodiment is typically a liquid crystal filter. But, it is not limited to the liquid crystal filter as long as the light shielding filter 211 is configured to be capable of switching transmission and shielding of light from the light source 30 for each image-capture area E. Further, an arbitrary range that transmission and shielding of light by the light shielding filter 211 can be switched may be set.

The information processing apparatus 260 includes hardware necessary for a computer such as a CPU (Central Processing Unit), a ROM (Read Only Memory), a RAM (Random Access Memory), and an HDD (Hard Disk Drive). In the present embodiment, for example, the image processing apparatus 260 is a PC (Personal Computer) or the like, but, the image processing apparatus 260 may be other arbitrary computer.

When the CPU loads a program of the present technology stored in the ROM or the HDD in the RAM and executes the program, the CPU controls operations of the respective blocks (described later) of the image processing apparatus 260. In the present embodiment, the information processing apparatus 260 controls of the operations of the image-capture mechanism 40 and the light shielding filter 211 and the light emission of the light source 30, to thereby capturing the images of the plurality of fertile ova F.

Figure 8:
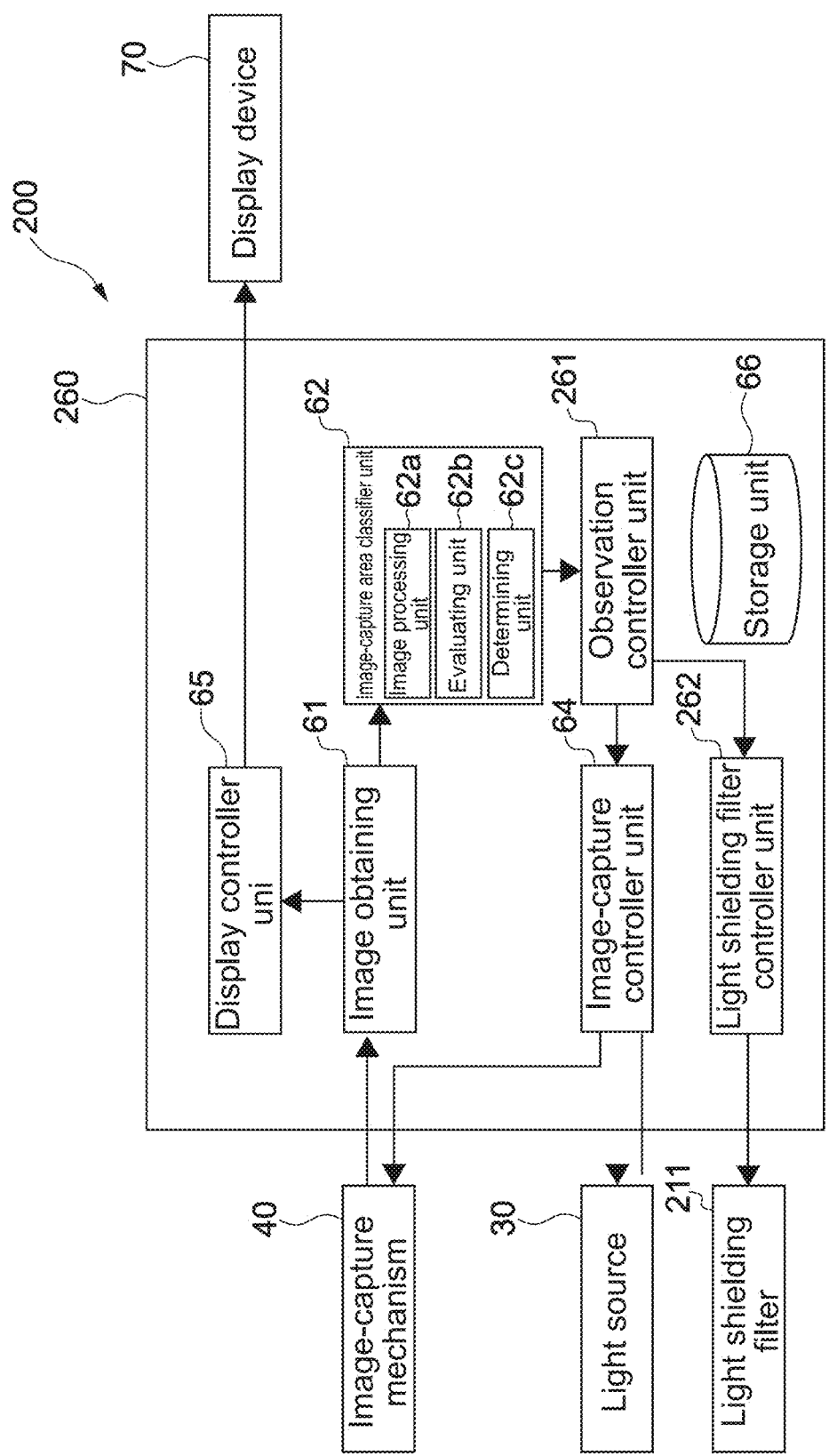
FIG. 8 is a function block diagram of the observation system.

Next, the configuration of the information processing apparatus 260 will be described. FIG. 8 is a function block diagram of the observation system 200.

As shown in FIG. 8, the information processing apparatus 260 includes the image obtaining unit 61, the image-capture area classifier unit 62, the image-capture controller unit 64, the display controller unit 65, the storage unit 66, the observation controller unit 261, and a light shielding filter controller unit 262.

The observation controller unit 261 controls the image-capture controller unit 64 and the light shielding filter controller unit 262 on the basis of the determination result of the determining unit 62c. The light shielding filter controller unit 262 controls the light shielding filter 211 such that transmission and shielding of light emitted from the light source 30 for each image-capture area E are switched on a basis of the instruction by the observation controller unit 261.

Effects of Light Shielding Filter

Figure 9:
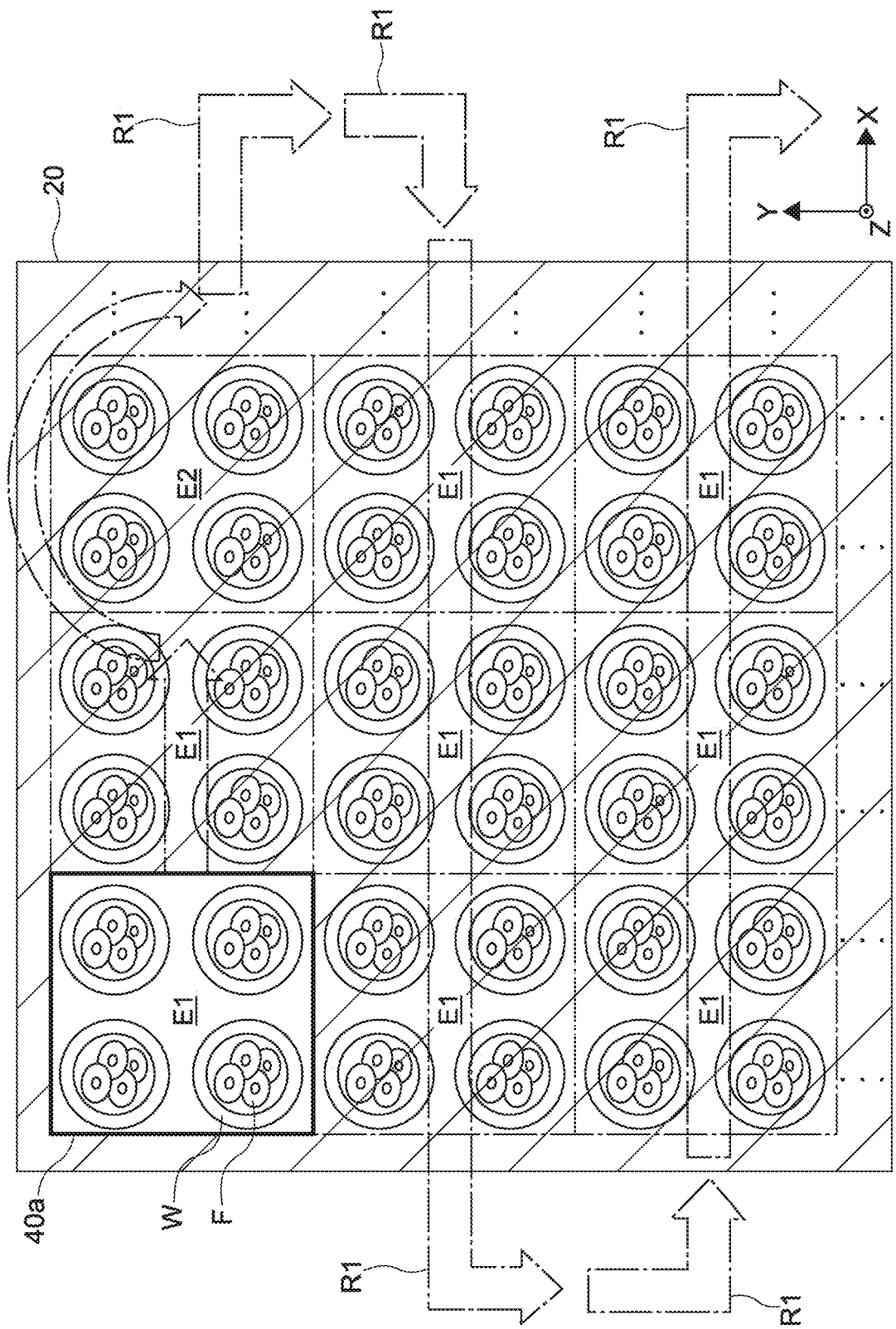
FIG. 9 is a diagram schematically showing a moving route of an image-capture mechanism of the observation system.

FIG. 9 schematically shows the moving route of the image-capture mechanism 40 according to a second embodiment and showing a state that the light from the light source 30 is locally transmitted by the light shielding filter 211. Note that a hatching area shown in FIG. 9 is an area of which the light from the light source 30 is shielded.

The light shielding filter 211 is controlled by the light shielding filter controller unit 262 to shield the light from light source 30 such that only the field-of-view range 40a of the image-capture mechanism 40 (first image-capture area E1) is irradiated with the light from the light source 30 when the image-capture mechanism 40 captures the images of the first image-capture area E1.

As a result, since the fertile ova F housed in the wells W in the image-capture areas E other than the first image-capture area E1 are not irradiated with light when the image-capture mechanism 40 captures the images of the first image-capture area E1, the photo-damages (phototoxicity) to the fertile ova F are reduced.

Modification Example

The configuration of the observation system 200 according to the second embodiment is not limited to the above-described method, and modification, addition, or the like may be performed, as appropriate.

For example, in the second embodiment, the light source 30 may be an illumination device configured to be capable of locally irradiating each of the plurality of image-capture areas E with light. As the illumination device, an illumination device including micro LEDs (Light Emitting Diodes) arrayed in a matrix corresponding to the field-of-view ranges 40a (image-capture areas E) of the image-capture mechanism 40 is used, for example.

By using the light source 30 that is the above-described illumination device, only the field-of-view range 40a (first image-capture area E1) of the image-capture mechanism 40 can be irradiated with light when the images of the first image-capture areas E1 are captured even if no light shielding filter 211 is provided between the light source 30 and the culture vessel 20. Thus, the above-described effects can be achieved. Note that, in a case where the light source 30 is the illumination device, the light shielding filter 211 may be provided to the observation system 200 or may be omitted.

Third Embodiment

Figure 10:
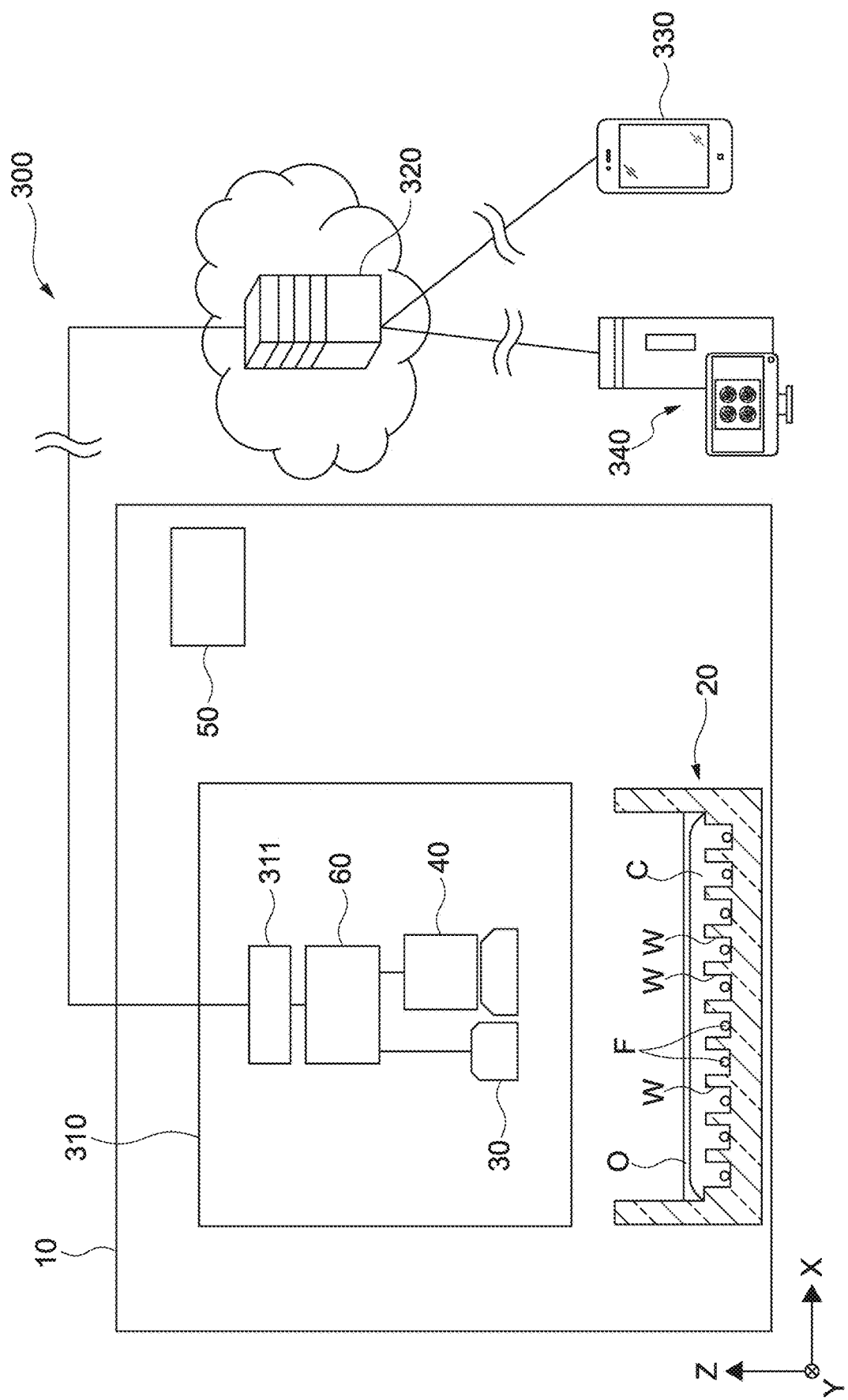
FIG. 10 is a diagram schematically showing a configuration example of an observation system according to a third embodiment of the present technology.

Next, an observation system 300 according to a third embodiment of the present technology will be described. FIG. 10 schematically shows a configuration example of the observation system 300 according to a third embodiment of the present technology. Hereinafter, configuration similar to the configuration of the first embodiment will be denoted by similar reference signs, and detailed description thereof will be omitted.

While in the observation system 100 according to the first embodiment, the culture vessel 20 and the image-capture mechanism 40 are arranged in the culturing device 10 and the information processing apparatus 60 is arranged outside the culturing device 10, in the observation system 300 according to the present embodiment, as shown in FIG. 10, the culture vessel 20, the image-capture mechanism 40, and the information processing apparatus 60 are arranged in the culturing device 10.

As shown in FIG. 10, the observation system 300 includes the culturing device 10, the culture vessel 20, and an image-capture mechanism/information processing apparatus integrated unit 310, and the gas controller unit 50. The image-capture mechanism/information processing apparatus integrated unit 310 is connected to a cloud server 320 via a network. Further, a mobile terminal 330 and a PC 340 are also connected to a cloud server 320 via a network.

As shown in FIG. 10, the image-capture mechanism/information processing apparatus integrated unit 310 is arranged in the culturing device 10. As shown in FIG. 10, the image-capture mechanism/information processing apparatus integrated unit 310 includes the image-capture mechanism 40, the light source 30, the information processing apparatus 60, and a communication unit 311. In this embodiment, the light source 30 is arranged vertical upward of the culture vessel 20.

The communication unit 311 receives the images of the plurality of fertile ova F stored in the information processing apparatus 60 from the information processing apparatus 60 and outputs the images to the cloud server 320 via the network.

The cloud server 320 stores the images of the plurality of fertile ova F. In addition, the PC 340 and the mobile terminal 330 are operated by a user, receive the plurality of fertile ova F from the cloud server 320 via the network, and display the images.

Other Embodiments

While the present technology is described herein with reference to the embodiments, it should be appreciated that the present technology is not limited thereto, and variations and modifications may be made.

For example, the image-capture controller unit 64 may control the number of times to capture the images of specific first image-capture areas E1 included in the plurality of image-capture areas E classified as the first image-capture areas by the image-capture mechanism 40. The specific first image-capture areas E1 according to the present embodiment are the image-capture areas E including the fertile ova F inherently having good quality such as fertile ova F taken from livestock of good strain and the like, for example.

Thus, for example, by utilizing a leftover time resulting from the omission of capturing the images of the second image-capture areas E2, the number of times to capture the images of the fertile ova F in the specific first image-capture areas E1 can be greater than the number of times to capture the images of the other first image-capture areas E1. As a result, as compared with the case that the images of all the fertile ova F housed in the culture vessel 20 are captured, the images of the fertile ova F of highly interest can be intensively captured. The images of the fertile ova F can be highly selectively captured.

Further, in the present embodiments, by using the evaluation values calculated in accordance with the machine learning algorithm and opinions from embryologists, it may switch the omission of capturing the images of the second image-capture areas E2 and intensive capturing of the images of the specific first image-capture areas E1.

In addition, in the observation systems 100 to 300, the fertile ova F housed in the wells W included in the image-capture areas E classified as the second image-capture areas E2 may be removed. As a result, a negative influence of the fertile ova F to be removed on the fertile ova F housed in the wells W of the first image-capture areas E1 can be suppressed.

Examples of the method of removing the fertile ova F housed in the wells W in the second image-capture areas E2 include a method of using an optical tweezers, a micropipette, or the like, a method of peeling bottoms of the wells W in the second image-capture areas E2 to physically drop off the fertile ova F housed in the wells W by using a cell removal mechanism provided on the culture vessel 20, and the like.

Further, the cells observed by the observation systems 100 to 300 according to the present technology are typically fertile ova. Not limited to these, they may be cells derived from livestock such as mouse, cow, pig, dog, cat, and the like, or ova and fertile ova of human or the like, for example.

The present technology may also have the following structures.

(1)
An information processing apparatus, including:
an image-capture controller unit that controls an image-capture mechanism to capture images of a culture vessel including a plurality of wells that house cells for each image-capture area;
an image-capture area classifier unit that applies image processing to the images captured by the image-capture mechanism and classifies the plurality of image-capture areas into a first image-capture area of which image-capturing is continued and a second image-capture area of which image-capturing is not continued on the basis of a result of the image processing; and
an observation controller unit that instructs the image-capture controller unit to capture an image of an image-capture area classified as the first image-capture area and not to capture an image of an image-capture area as the second image-capture area.

(2)
The information processing apparatus according to (1), in which
the image-capture area classifier unit includes
an evaluating unit that evaluates whether or not each of the plurality of wells included in each of the image-capture area is suitable for observation, and
a determining unit that determines the image-capture area as the first image-capture area or the second image-capture area on the basis of an evaluation result of the evaluating unit.

(3)
The information processing apparatus according to (2), in which
the determining unit determines the image-capture area as the second image-capture area in a case where all wells included in the image-capture area are unsuitable for observation and determines the image-capture area as the first image-capture area in a case where at least one well included in the image-capture area is suitable for observation.

(4)
The information processing apparatus according to (2) or (3), in which
the evaluating unit evaluates whether or not the wells are suitable for observation in accordance with a growing state of the cells housed in the wells.

(5)
The information processing apparatus according to any one of (2) to (4), in which
the evaluating unit evaluates the growing state of the cells in accordance with machine learning algorithm.

(6)
The information processing apparatus according to any one of (2) to (5), in which
the evaluating unit evaluates the wells each of which houses one cell as the wells suitable for observation and the wells that house the plurality of cells and the wells that house no cells as the wells unsuitable for observation.

(7)
The information processing apparatus according to any one of (1) to (6), in which
the observation controller unit instructs the image-capture controller unit such that the number of times of capturing the images of a specific first image-capture area included in the plurality of image-capture areas classified as the first image-capture area is greater than the number of times of capturing the images of a first image-capture area other than the specific first image-capture area.

(8)
The information processing apparatus according to any one of (1) to (7), in which
the image-capture controller unit changes a first moving route along which the image-capture mechanism passes through all the plurality of image-capture areas to a second moving route shorter than the first moving route on the basis of an instruction by the observation controller unit.

(9)
An information processing method, including:
controlling an image-capture mechanism to capture images of a culture vessel including a plurality of wells that house cells for each image-capture area;
applying image processing to the images captured by the image-capture mechanism and classifying the plurality of image-capture areas into a first image-capture area of which image-capturing is continued and a second image-capture area of which image-capturing is not continued on the basis of a result of the image processing; and
instructing the image-capture controller unit to capture an image of an image-capture area classified as the first image-capture area and not to capture an image of an image-capture area as the second image-capture area.

(10)
A program, that causes the image processing apparatus according to any one of (1) to (8) to execute the steps of:
controlling an image-capture mechanism to capture images of a culture vessel including a plurality of wells that house cells for each image-capture area;
applying image processing to the images captured by the image-capture mechanism and classifying the plurality of image-capture areas into a first image-capture area of which image-capturing is continued and a second image-capture area of which image-capturing is not continued on the basis of a result of the image processing; and instructing the image-capture controller unit to capture an image of an image-capture area classified as the first image-capture area and not to capture an image of an image-capture area as the second image-capture area.

(11)

An observation system, including:

a culture vessel including a plurality of wells that house cells;

an image-capture mechanism that captures images of the culture vessel for each image-capture area;

a light source that irradiates the culture vessel with light; and an information processing apparatus, including an image-capture controller unit that controls the image-capture mechanism, an image-capture area classifier unit that applies image processing to the images captured by the image-capture mechanism and classifies the plurality of image-capture areas into a first image-capture area of which image-capturing is continued and a second image-capture area of which image-capturing is not continued on the basis of a result of the image processing, and an observation controller unit that instructs the image-capture controller unit to capture an image of an image-capture area classified as the first image-capture area and not to capture an image of an image-capture area as the second image-capture area.

(12)

The observation system according to (11), further including:

a light shielding filter that shields light such that only a field-of-view range of the image-capture mechanism is irradiated with the light from the light source at a time of capturing the images of the first image-capture area by the image-capture mechanism.

(13)

The observation system according to (11) or (12), in which the light source is an illumination device configured to be capable of locally irradiating each of the plurality of image-capture areas with light, the illumination device irradiating only the field-of-view range of the image-capture mechanism with light at a time of capturing the images of the first image-capture area by the image-capture mechanism.

(14)

The observation system according to any one of (11) to (13), in which the culture vessel includes a cell removal mechanism configured to be capable of removing cells housed in the wells included in the image-capture area classified as the second image-capture area.

REFERENCE SIGNS LIST

100, 200, 300 observation system
20 culture vessel
30 light source
40 image-capture mechanism
60, 260 information processing apparatus
62 image-capture area classifier unit
62b evaluating unit
62c determining unit
63, 261 observation controller unit
64 image-capture controller unit
211 light shielding filter E image-capture area
E1 first image-capture area
E2 second image-capture area
F fertile ovum (cell)
W well

The invention claimed is:

1. An information processing apparatus comprising:
circuitry configured to:
obtain images of a culture vessel including a plurality of wells that house cells for each image-capture area, the images being captured by an image capture mechanism;
determine if a well houses a cell on a basis of the images captured by the image capture mechanism and classify the plurality of image-capture areas into a first image-capture area of which image-capturing is continued and a second image-capture area of which image-capturing is not continued on a basis of the determination; and
control the image capture mechanism to capture an image of an image-capture area classified as the first image-capture area and not to capture an image of an image-capture area classified as the second image-capture area in response to a determination if a well houses a cell and a classification of the plurality of image-capture areas, the image capture mechanism further configured to capture images of the first image-capture area without regard to subsequent determinations if a well houses a cell;
wherein the circuitry is further configured to instruct the image capture mechanism to further capture the image-capture area classified as the first image-capture area during a time interval previously used to capture an image-capture area classified as the second image-capture area;
wherein the circuitry is further configured to determine whether a well in the first image-capture area houses more than one cell and to instruct the image capture mechanism to capture an image of a well in the first image-capture area only if the well houses a single cell;
wherein the circuitry is further configured to evaluate whether or not each of the plurality of wells included in each of the image-capture area is suitable for observation, and
determine the image-capture area as the first image-capture area or the second image-capture area on a basis of an evaluation result;
wherein the circuitry is further configured to evaluate whether or not the wells are suitable for observation in accordance with a growing state of the cells housed in the wells; and
wherein the circuitry is further configured to evaluate the growing state of the cells in accordance with machine learning algorithm.

2. The information processing apparatus according to claim 1, wherein
the circuitry is further configured to determine the image-capture area as the second image-capture area in a case where all wells included in the image-capture area are unsuitable for observation and determines the image-capture area as the first image-capture area in a case where at least one well included in the image-capture area is suitable for observation.

3. The information processing apparatus according to claim 1, wherein
the circuitry is further configured to evaluate the wells and the wells that house one cell and the wells that house the plurality of cells are the wells suitable for observation and the wells that house no cells are the wells unsuitable for observation.

4. The information processing apparatus according to claim 1, wherein
the circuitry is further configured to instruct the image capture mechanism such that a number of times of capturing the images of a specific first image-capture area included in the plurality of image-capture areas classified as the first image-capture area is greater than a number of times of capturing the images of a first image-capture area other than the specific first image-capture area.

5. The information processing apparatus according to claim 1, wherein
the circuitry is further configured to change a first moving route along which the image-capture mechanism passes through all the plurality of image-capture areas to a second moving route shorter than the first moving route.

6. An information processing method, comprising:
obtaining images of a culture vessel including a plurality of wells that house cells for each image-capture area, the images being captured by an image capture mechanism;
determining if a well houses a cell on a basis of the images captured by the image capture mechanism and classify the plurality of image-capture areas into a first image-capture area of which image-capturing is continued and a second image-capture area of which image-capturing is not continued on a basis of the determination; and
controlling the image capture mechanism to capture an image of an image-capture area classified as the first image-capture area and not to capture an image of an image-capture area classified as the second image-capture area in response to determining if a well houses a cell and a classification of the plurality of image-capture areas, the image capture mechanism further configured to capture images of the first image-capture area without regard to subsequent determinations if a well houses a cell;
wherein the circuitry is further configured to instruct the image capture mechanism to further capture the image-capture area classified as the first image-capture area during a time interval previously used to capture an image-capture area classified as the second image-capture area;
wherein the circuitry is further configured to determine whether a well in the first image-capture area houses more than one cell and to instruct the image capture mechanism to capture an image of a well in the first image-capture area only if the well houses a single cell;
wherein the circuitry is further configured to evaluate whether or not each of the plurality of wells included in each of the image-capture area is suitable for observation, and
determine the image-capture area as the first image-capture area or the second image-capture area on a basis of an evaluation result;
wherein the circuitry is further configured to evaluate whether or not the wells are suitable for observation in accordance with a growing state of the cells housed in the wells; and
wherein the circuitry is further configured to evaluate the growing state of the cells in accordance with machine learning algorithm.

7. A non-transitory computer readable storage medium having computer executable instructions stored thereon that, when executed by an image processing apparatus, cause the image processing apparatus to execute the steps of:
obtaining images of a culture vessel including a plurality of wells that house cells for each image-capture area, the images being captured by an image capture mechanism;
determining if a well houses a cell on a basis of the images captured by the image capture mechanism and classify the plurality of image-capture areas into a first image-capture area of which image-capturing is continued and a second image-capture area of which image-capturing is not continued on a basis of the determination; and
controlling the image capture mechanism to capture an image of an image-capture area classified as the first image-capture area and not to capture an image of an image-capture classified area as the second image-capture area in response to determining if a well houses a cell and a classification of the plurality of image-capture areas, the image capture mechanism further configured to capture images of the first image-capture area without regard to subsequent determinations if a well houses a cell;
wherein the circuitry is further configured to instruct the image capture mechanism to further capture the image-capture area classified as the first image-capture area during a time interval previously used to capture an image-capture area classified as the second image-capture area;
wherein the circuitry is further configured to determine whether a well in the first image-capture area houses more than one cell and to instruct the image capture mechanism to capture an image of a well in the first image-capture area only if the well houses a single cell;
wherein the circuitry is further configured to evaluate whether or not each of the plurality of wells included in each of the image-capture area is suitable for observation, and
determine the image-capture area as the first image-capture area or the second image-capture area on a basis of an evaluation result;
wherein the circuitry is further configured to evaluate whether or not the wells are suitable for observation in accordance with a growing state of the cells housed in the wells; and
wherein the circuitry is further configured to evaluate the growing state of the cells in accordance with machine learning algorithm.

8. An observation system, comprising:
an image-capture mechanism that captures images of wells for each image-capture area;
a light source that irradiates the wells with light; and
an information processing apparatus configured to obtain images of the wells that house cells for each image-capture area, the images being captured by the image capture mechanism, determine if a well in the plurality of wells houses a cell on a basis of the images captured by the image capture mechanism and classify the plurality of image-capture areas into a first image-capture area of which image-capturing is continued and a second image-capture area of which image-capturing is not continued on a basis of the determination, and control the image capture mechanism to capture an image of an image-capture area classified as the first image-capture area and not to capture an image of an image-capture area classified as the second image-capture area in response to a determination if a well houses a cell and a classification of the plurality of image-capture areas, the image capture mechanism further configured to capture images of the first image-capture area without regard to subsequent determinations if a well houses a cell;

wherein the circuitry is further configured to instruct the image capture mechanism to further capture the image-capture area classified as the first image-capture area during a time interval previously used to capture an image-capture area classified as the second image-capture area;

wherein the circuitry is further configured to determine whether a well in the first image-capture area houses more than one cell and to instruct the image capture mechanism to capture an image of a well in the first image-capture area only if the well houses a single cell;

wherein the circuitry is further configured to evaluate whether or not each of the plurality of wells included in each of the image-capture area is suitable for observation, and determine the image-capture area as the first image-capture area or the second image-capture area on a basis of an evaluation result;

wherein the circuitry is further configured to evaluate whether or not the wells are suitable for observation in accordance with a growing state of the cells housed in the wells; and wherein the circuitry is further configured to evaluate the growing state of the cells in accordance with machine learning algorithm.

9. The observation system according to claim 8, further comprising:

a light shielding filter that shields light such that only a field-of-view range of the image-capture mechanism is irradiated with the light from the light source at a time of capturing the images of the first image-capture area by the image-capture mechanism.

10. The observation system according to claim 8, wherein the light source is an illumination device configured to locally irradiate each of the plurality of image-capture areas with light, the illumination device irradiating only the field-of-view range of the image-capture mechanism with light at a time of capturing the images of the first image-capture area by the image-capture mechanism.

11. The observation system according to claim 8, including a cell removal mechanism configured to remove cells housed in the wells included in the image-capture area classified as the second image-capture area.

12. The observation system according to claim 8, further comprising a culture vessel containing the plurality of wells.

* * * * *